United States Patent [19]

Clemence et al.

[11] 4,224,333
[45] Sep. 23, 1980

[54] ANTIHYPERTENSIVE 2H-INDOL-2-ONES

[75] Inventors: François Clemence, Paris; Daniel Humbert, Fontenay-sous-Bois; Robert Fournex, Paris, all of France

[73] Assignee: Roussel Uclaf, Paris, France

[21] Appl. No.: 21,243

[22] Filed: Mar. 15, 1979

[30] Foreign Application Priority Data

Mar. 22, 1978 [FR] France .................... 78 08292

[51] Int. Cl.² .................... A61K 31/445; C07D 405/14
[52] U.S. Cl. .................... 424/267; 546/197; 546/201; 546/216; 260/340.3
[58] Field of Search .................... 546/201, 197; 424/267; 260/326.11 R

[56] References Cited

U.S. PATENT DOCUMENTS

| 3,644,403 | 2/1972 | Canas-Rodriguez et al. | 260/326.11 R |
| 3,720,670 | 3/1973 | Nakanishi et al. | 546/197 X |
| 3,850,938 | 11/1974 | Derible et al. | 546/201 |
| 3,947,578 | 3/1976 | Derible et al. | 424/267 |
| 4,100,291 | 7/1978 | Clemence et al. | 546/201 X |

FOREIGN PATENT DOCUMENTS 2213059  8/1974  France .................... 546/199

*Primary Examiner*—Henry R. Jiles
*Assistant Examiner*—Richard A. Schwartz
*Attorney, Agent, or Firm*—Hammond & Littell, Weissenberger and Muserlian

[57] ABSTRACT

Novel optically active isomers or racemates of 1,3-dihydro-3-{1-[2-(2,3-dihydro-1,4-benzodioxin-2-yl)-2-hydroxyethyl]-piperidin-4-yl}-2H-indol-2-ones of the formula

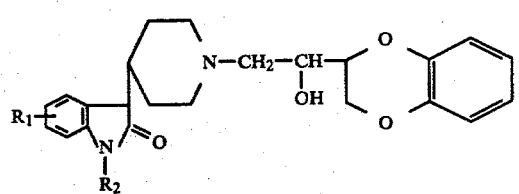

wherein $R_1$ is selected from the group consisting of hydrogen, chlorine, bromine, fluorine and alkoxy of 1 to 5 carbon atoms and $R_2$ is selected from the group consisting of hydrogen and alkyl of 1 to 5 carbon atoms and their non-toxic, pharmaceutically acceptable acid addition salts having antihypertensive activity and a novel process and intermediates for their preparation.

18 Claims, No Drawings

ANTIHYPERTENSIVE 2H-INDOL-2-ONES

STATE OF THE ART

Related, but non-anticipating, prior art are French Pat. Nos. 2,349,331 and 2,213,059 and commonly assigned U.S. Pat. Nos. 3,850,938 and 3,947,578.

OBJECTS OF THE INVENTION

It is an object of the invention to provide the novel compounds of formula I and their non-toxic, pharmaceutically acceptable acid addition salts.

It is another object of the invention to provide a novel process for the preparation of the compounds of formula I and novel intermediates formed therein.

It is a further object of the invention to provide novel antihypertensive compositions and to provide a novel method of treating hypertension in warm-blooded animals.

THE INVENTION

The novel compounds of the invention are selected from the group consisting of optically active isomers or racemates of 1,3-dihydro-3-{1-[2-(2,3-dihydro-1,4-benzodioxin-2-yl)-2-hydroxyethyl]-piperidin-4-yl}-2H-indol-2-ones of the formula

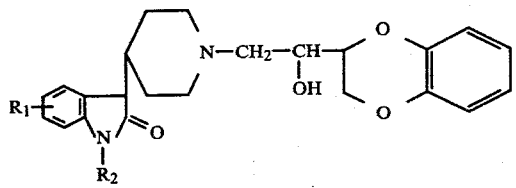

wherein $R_1$ is selected from the group consisting of hydrogen, chlorine, bromine, fluorine and alkoxy of 1 to 5 carbon atoms and $R_2$ is selected from the group consisting of hydrogen and alkyl of 1 to 5 carbon atoms and their non-toxic, pharmaceutically acceptable acid addition salts.

Examples of alkyl groups for $R_2$ are methyl, ethyl, propyl, isopropyl, butyl, sec-butyl, tert.-butyl and pentyl. Examples of alkoxy groups of $R_1$ are methoxy, ethoxy, propoxy, isopropoxy, butoxy, sec-butoxy, tert.-butoxy and pentoxy.

Examples of suitable acids for the non-toxic, pharmaceutically acceptable acid addition salts are inorganic acids such as hydrochloric acid, hydrobromic acid, hydroiodic acid, nitric acid, sulfuric acid and phosphoric acid and organic acids such as formic acid, acetic acid, benzoic acid, maleic acid, fumaric acid, succinic acid, tartaric acid, citric acid, oxalic acid, glyoxylic acid and aspartic acid, alkyl monosulfonic acids and alkyl disulfonic acids such as methane sulfonic acid, ethane sulfonic acid, propane sulfonic acid, methane disulfonic acid and $\alpha,\beta$-ethane disulfonic acid and aryl monosulfonic acids and aryl disulfonic acids such as benzene sulfonic acid.

Among the preferred compounds of the invention are the optical isomers and racemates of the compounds of formula I wherein $R_1$ is hydrogen, chlorine or methoxy and $R_2$ is hydrogen or methyl and their non-toxic, pharmaceutically acceptable acid addition salts.

Examples of specific compounds of the invention are optical isomers and racemates of erythro 1,3-dihydro-3-{1-[2-(2,3-dihydro-1,4-benzodioxin-2-yl)-2- hydroxyethyl]-piperidin-4-yl}-2H-indol-2-one and its hydrochloride, of threo 1,3-dihydro-3-{1-[2-(2,3-dihydro-1,4-benzodioxin-2-yl)-2-hydroxyethyl]-piperidin-4-yl}-2H-indol-2-one and its hydrochloride, of erythro 1,3-dihydro-3-{1-[2-(2,3-dihydro-1,4-benzodioxin-2-yl)-2-hydroxyethyl]-piperidin-4-yl}-1-methyl-2H-indol-2-one and its hydrochloride and of erythro 1,3-dihydro-3-{1-[2-(2,3-dihydro-1,4-benzodioxin-2yl)-2-hydroxyethyl]-piperidin-4-yl}-5-methoxy-2H-indol-2-one and its hydrochloride.

The novel process of the invention for the preparation of a compound of formula I comprises reacting a compound of the formula

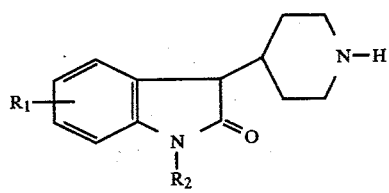

wherein $R_2$ and $R_1$ have the above definition with a compound of the formula

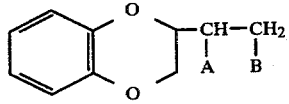

wherein A and B together represent an oxygen atom or A is —OH and B is selected from the group consisting of chlorine or bromine to obtain the corresponding compound of formula I and which, if desired, may be salified with an organic or inorganic acid to form the non-toxic, pharmaceutically acceptable acid addition salt thereof.

In a preferred mode of the process of the invention, A and B together are an oxygen atom and the reaction is effected in an organic solvent such as aromatic hydrocarbons like benzene, toluene and xylene; alkanols like methanol, ethanol or propanol, a halogenated hydrocarbon like methylene chloride, chloroform or an analogous or mixtures of solvents such as a mixture of an aromatic hydrocarbon and a lower alkanol. When A is hydroxy and B is halogen, the reaction is effected in an organic solvent such as aromatic hydrocarbons like benzene, toluene and xylene; lower alkanols such as ethanol, butanol and amyl alcohol; ketones like acetone, methyl ethyl ketone and methyl isobutyl ketone; ethers such as dioxane; or amides like dimethylformamide. Preferably an excess of the product of formula III is used.

The reaction is preferably effected in the presence of a basic agent such as an alkali metal carbonate or an alkali metal bicarbonate and is effected at a temperature ranging from room temperature to reflux temperatures of the reaction mixture. The products of formulae II and III may be used in any one of their isomeric forms.

The salification of the products of formula I may be effected by reacting substantially stoichiometric amounts of the acid and the compound of formula I in one or more solvents such as water, ether or acetone.

The products of formula I can exist in different form of stereochemical optical isomers and the invention is equally directed to the different forms that may be separated from their racemates by known procedures. the diastereoisomeric racemates designated as erythro and threo can be separated by known methods such as selective crystallization, column chromatography or by directed preparation of the compound of formula I using the desired form of the compounds of formulae II and/or III.

The erythro and threo racemates may be resolved into their optical enantiomorphs by known methods such as formation of salts of optically active acids. It is intended that the mixtures of the different isomers of formula I and especially mixtures of diastereoisomeric racemates are included with the invention.

The novel process of the invention for the preparation of compounds of formula II comprises reacting a compound of the formula

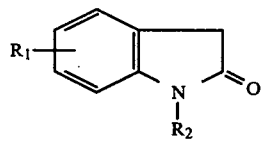
A wherein $R_1$ and $R_2$ have the above definitions with a compound of the formula

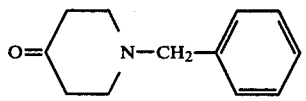
B to form a compound of the formula

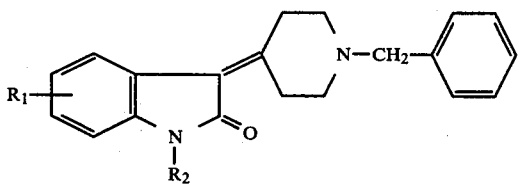
IV and reacting the latter with a reducing and debenzylating agent to obtain the compound of formula II.

In a preferred mode of the latter process, the reaction of compounds A and B is effected in an organic solvent such as alkanol like methanol, ethanol or propanol in the presence of a basic agent such as ammonia or an amine such as monoethylamine, diethylamine, triethylamine, pyrrolidine or piperidine. The reaction temperature may vary from room temperature to reflux of the reaction mixture. The preferred debenzylation and reduction agent is hydrogen in the presence of a catalyst such as platinum or palladium and the reaction is preferably effected in an organic solvent such as an acid like acetic acid or an alkanol such as methanol, ethanol or propanol.

The novel antihypertensive compositions of the invention are comprised of an antihypertensively effective amount of at least one compound of formula I and their non-toxic, pharmaceutically acceptable acid addition salts and an inert pharmaceutical carrier or excipient. The compositions may be in the form of tablets, dragees, gelules, granules, suppositories or injectable solutions or suspensions.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants or emulsifiers and preservatives.

The compositions are able to lower blood pressure and are therefore useful for the treatment of various forms of arterial hypertension; namely permanent, slight, moderate or severe.

Among the preferred compositions of the invention are the optical isomers and racemates of the compounds wherein $R_1$ is hydrogen, chlorine or methoxy and $R_2$ is hydrogen or methyl and their non-toxic, pharmaceutically acceptable acid addition salts.

Examples of specific compounds for the compositions are optical isomers and racemates of erythro 1,3-dihydro-3-{1-[2-(2,3-dihydro-1,4-benzodioxin-2-yl)-2-hydroxyethyl]-piperidin-4-yl}-2H-indol-2-one and its hydrochloride, of threo 1,3-dihydro-3-{1-[2-(2,3-dihydro-1,4-benzodioxin-2-yl)-2-hydroxyethyl]-piperidin-4-yl}-2H-indol-2-one and its hydrochloride, of erythro 1,3-dihydro-3-{1-[2-(2,3-dihydro-1,4-benzodioxin-2-yl)-2-hydroxyethyl]-piperidin-4-yl}-1-methyl-2H-indol-2-one and its hydrochloride and of erythro 1,3-dihydro-3-{1-[2-(2,3-dihydro-1,4-benzodioxin-2-yl)-2-hydroxyethyl]-piperidin-4-yl}-5-methoxy-2H-indol-2-one and its hydrochloride.

The novel method of treating hypertension in warm-blooded animals, including humans, comprises administering to warm-blooded animals an hypertensively effective amount of at least one compound of formula I and their non-toxic, pharmaceutically acceptable acid addition salts. The compositions may be administered orally, rectally or parenterally, preferably orally, and the usual daily dose is 2 to 4.0 mg/kg depending on the compound and the method of administration.

The novel intermediates compounds of the invention are the compounds of formulae II and IV and especially 1,3-dihydro-1-methyl-3-(piperidin-4-yl)-2H-indol-2-one, 5-methoxy-3-(piperidin-4-yl)-2H-indol-2-one, 1,3-dihydro-1-methyl-3-(1-benzyl-4-piperidylene)-2H-indol-2-one and 5-methoxy-3-(1-benzyl-4-piperidylene)-2H-indol-2-one.

In the following examples there are described several preferred embodiments to illustrate the invention. However, it should be understood that the invention is not intended to be limited to the specific embodiments.

EXAMPLE 1

3-{1-[2-(2,3-dihydro-1,4-benzodioxin-2-yl)-2-hydroxyethyl]-piperidin-4-yl}-1,3-dihydro-2H-indol-2-one.HCl STEP A: 3-(1-benzyl-4-piperidylene)-2H-indol-2-one Ammonia was bubbled with stirring through a mixture of 20 g of indol-2-one, 29.2 g of N-benzyl-4-piperidone and 420 ml of ethanol for 30 minutes and the mixture was heated at 80°–90° C. for 2 hours to reduce the volume of ethanol by one half. The solution was cooled and 200 ml of water were added thereto. The mixture was filtered and the recovered product was washed with a 1-1 water-methanol mixture and was dried to obtain 34 g of 3-(1-benzyl-4-piperidylene)-2H-indol-2-one which melted at 218° C. after crystallization from xylene.

STEP B: 3-(piperidin-4-yl)-2H-indol-2-one

A mixture of 38.1 g of the product of Step A, 4 g of 10% palladized carbon and 250 ml of acetic acid were reacted at 50° C. in a hydrogenation cell and at the end of the reaction, the mixture was filtered. The filtrate was evaporated to dryness and the residue was taken up in 500 ml of water. The mixture was made alkaline with sodium hydroxide and was extracted six times with 200 ml of ether after saturating the aqueous phase with sodium chloride. The ether phase was dried over sodium sulfate and was evaporated to dryness. The oil residue with a boiling point of 192°-194° C. was distilled to obtain 11 g of amorphous 3-(piperidin-4-yl)-2H-indol-2-one. The process was repeated a second time under the same conditions and the raw product was dissolved in hot benzene and was precipitated by addition of cyclohexane to obtain the said product with a melting point of 156° C.

STEP C:
3-{1-[2-(2,3-dihydro-1,4-benzodioxin-2-yl)-2-hydroxyethyl]-piperidin-4-yl}-1,3-dihydro-2H-indol-2-one hydrochloride A mixture of 8.9 g of a mixture of two threo and erythro racemates of 2,3-dihydro-2-oxiranyl-1,4-benzodioxin, 8.7 g of the product of Step B, 100 ml of anhydrous benzene, 2 ml of methanol and 0.1 g of hydroquinone was refluxed for 2 hours and the benzene and methanol were evaporated under reduced pressure. The residue was taken up in 20 ml of ethyl acetate and the mixture was held in a refrigerator for 3 days to obtain 8.6 g of product. The latter was crystallized from 40 ml of the isopropanol to obtain 6 g of 3-{1-[2-(2,3-dihydro-1,4-benzodioxin-2-yl)-2-hydroxyethyl]-piperidin-4-yl}-1,3-dihydro-2H-indol-2-one melting at 115°-120° C.

Analysis: $C_{23}H_{26}N_2O_4$; Calculated: %C: 70.03; %H: 6.64; %N: 7.10; Found: %C: 69.8; %H: 7.0; %N: 6.9.
NMR Spectrum (deuterochloroform—60 MHz): peaks at 416 Hz

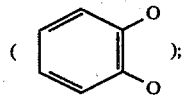

at 410-450 Hz (other aromatics); at 220-275 Hz (CH₂O— and —CHO); at 530 and 207 Hz (mobile hydrogens); at 80 to 195 Hz (other protons).

The said 6 g of free base were dissolved in 100 ml of acetone and 4.5 ml of 5 N hydrogen chloride in ether were added thereto. The mixture was evaporated to dryness under reduced pressure and the raw residue was taken up in 100 ml of hot ethanol to obtain 4.3 g of the hydrochloride of the said base melting at 160° C.

Analysis: $C_{23}H_{27}ClN_2O_4$;
Calculated: %C: 64.10; %H: 6.32; %N: 6.50; %Cl: 8.23; Found: %C: 63.8; %H: 6.7; %N 6.3; %Cl: 8.4.

EXAMPLE 2

(dl) erythro 1,3-dihydro-3-{1-[2-(2,3-dihydro-1,4-benzodioxin-2-yl)-2-hydroxyethyl]-piperidin-4-yl}-2H-indol-2-one hydrochloride A mixture of 4.35 g of 3-(4-piperidin-4-yl)-2H-indol-2-one, 4.5 g of (dl) erythro 2,3-dihydro-2-oxiranyl-1,4-benzodioxin, 50 ml of benzene and 5 ml of methanol was refluxed with stirring for 4 hours and after cooling the mixture, it was evaporated to dryness under reduced pressure. The 8.1 g of residue were chromatographed over silica gel and was eluted with a 95-5 methylene chloride-methanol mixture to obtain after crystallization overnight in a refrigerator 5.1 g of (dl) erythro 1,3-dihydro-3-{1-[2-(2,3-dihydro-1,4-benzodioxin-2-yl)-2-hydroxyethyl]-piperidin-4-yl}-2H-indol-2-one melting at 90°-100° C.

NMR Spectrum (deuterochloroform—60 MHz):
peaks at 200 to 270 Hz (—CH₂O and >CHO—); at 80 to 190 Hz (—CH₂ and angular hydrogen); at ≃410 Hz

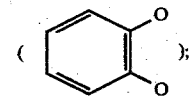

at 410 to 440 Hz (other aromatics).

The 5.1 g of the base were dissolved in 20 ml of isopropanol and 3 ml of 5 N hydrogen chloride in ether were added thereto. The mixture was evaporated to dryness under reduced pressure and the residue was taken up in 100 ml of ether. After stirring the mixture for 48 hours, it was vacuum filtered and the recovered product was washed with ether and dried to obtain the hydrochloride of the said base.

Analysis: $C_{23}H_{27}ClN_2O_4$
Calculated: %C: 64.10; %H: 6.32; %Cl: 8.23; %N: 6.50; Found: %C: 64.0; %H: 6.5; %Cl: 8.0; %N: 6.2.

EXAMPLE 3

(dl) threo 1,3-dihydro-3-{1-[2-(2,3-dihydro-1,4-benzodioxin-2-yl)-2-hydroxyethyl]-piperidin-4-yl}-2H-indol-2-one hydrochloride A mixture of 8.7 g of 3-(4-piperidinyl)-2H-indol-2-one, 8.6 g of (dl) threo 2,3-dihydro-2-oxiranyl-1,4-benzodioxin, 100 ml of benzene and 10 ml of methanol was refluxed for 18 hours and then 10 ml of 4N hydrogen chloride in ether were added thereto. The solvents were decanted and the product was crystallized from 30 ml of isopropyl alcohol to obtain 17.2 g of (dl) threo 1,3-dihydro-3-{1-[2-(2,3-dihydro-1,4-benzodioxin-2-yl)-2-hydroxyethyl]-piperidin-4-yl}-2H-indol-2-one melting at ≃180° C. The latter base was dissolved in 200 ml of hot methanol and the solution was filtered and returned to room temperature. 400 ml of hydrogen chloride in ether were added thereto and the mixture was vacuum filtered. The recovered product was dried to obtain 7.35 g of the hydrochloride of the base melting at ≃205° C.

Analysis: $C_{23}H_{27}ClN_2O_4$
Calculated: %C: 64.10; %H: 6.31; %Cl: 8.22; %N: 6.50; Found: %C: 63.7; %H: 6.6; %Cl: 8.1; %N: 6.2.
NMR Spectrum (DMSO—90 MHz):
peaks at 946-810-810-540-546 Hz (mobile hydrogens); at 615 to 660 Hz with peak at 618 Hz (aromatics); at 350 to 400 Hz (—CH₂O— and —CH—O); at 250 to 320 Hz (CH₂—N); at 125 to 220 Hz (other protons).

EXAMPLE 4

(dl) erythro 1,3-dihydro-3-{1-[2-(2,3-dihydro-1,4-benzodioxin-2-yl)-2-hydroxyethyl]-piperidin-4-yl}-1-methyl-2H-indol-2-one.HCl

STEP A:
1,3-dihydro-1-methyl-3-(1-benzyl-piperidin-4-ylidene)-2H-indol-2-one Ammonia was bubbled at room temperature for 2 hours through a mixture of 67 g of N-methyl-indol-2-one, 95 g of N-benzyl-4-piperidone and 1000 ml of ethanol and the mixture stood overnight and was then refluxed for 8 hours while maintaining a slight current of ammonia. The mixture was evaporated to dryness under reduced pressure and the residue was taken up in 500 ml of 2 N hydrochloric acid. The mixture was filtered and the recovered hydrochloride was washed with water and taken up in a mixture of 1 liter of water and 500 ml of ether. 100 ml of concentrated sodium hydroxide were added thereto and the mixture was stirred for 5 hours. The decanted organic phase was washed with water, was dried and evaporated to dryness to obtain 91 g of residue which was crystallized from 250 ml of isopropyl ether to obtain 59.7 g of 1,3-dihydro-1-methyl-3-(1-benzyl-piperidin-4-ylidene)-2H-indol-2-one melting at 101° to 102° C.

Analysis:
Calculated: %C: 79.21; %H: 6.96; %N: 8.80; Found: %C: 78.9; %H: 7.0; %N: 8.7.

STEP B: 1,3-dihydro-3-(piperidin-4-yl)-2H-indol-2-one

A mixture of 16 g of the product of Step A, 150 ml of acetic acid and 2 g of 10% palladized carbon was saturated with hydrogen at 50° C. for 2 hours and after the reaction was finished, the mixture was filtered. The filtrate was evaporated to dryness and the residue was taken up in water. The mixture was made alkaline with concentrated sodium hydroxide solution and was extracted 4 times with 100 ml of methylene chloride. The combined organic phases were washed with a little water, dried and evaporated to dryness to obtain 9.5 g of 1,3-dihydro-3-(piperidin-4-yl)-2H-indol-2-one melting at ≃80° C.

Analysis:
Calculated: %C: 73.01; %H: 7.88; %N: 10.16; Found: %C: 72.6; %H: 7.8; %N: 11.8.

STEP C: (dl) erythro
1,3-dihydro-3-{1-[2-(2,3-dihydro-1,4-benzodioxin-2-yl)-2-hydroxyethyl]-piperidin-4-yl}-1-methyl-2H-indol-2-one hydrochloride A mixture of 9.2 g of the product of Step B, 8.6 g of erythro 2-oxyranyl-2,3-dihydro-1,4-benzodioxin, 100 ml of anhydrous benzene and 10 ml of methanol was refluxed with stirring for 20 hours and the mixture was evaporated to dryness under reduced pressure. The residue was chromatographed under pressure over silica gel and was eluted with a 96-4 methylene chloride-methanol mixture to obtain 11.4 g of raw (dl) erythro 1,3-dihydro-3-{1-[2-(2,3-dihydro-1,4-benzodioxin-2-yl)-2-hydroxyethyl]-piperidin-4-yl}-1-methyl-2H-indol-2-one.

Analysis: $C_{24}H_{28}N_2O_4$
Calculated: %C: 70.55; %H: 6.91; %N: 6.86; Found: %C: 70.8; %H: 6.9; %N: 6.8.
NMR Spectrum (deuterochloroform—60 MHz): peaks at 190.5 Hz (N—CH$_3$); at 210 to 270 Hz (—CHO and CH$_2$—O—); at 203–209 Hz

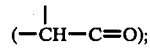

$(-CH-C=O)$;

at 75 to 180 Hz (other protons).

11 g of the said base were dissolved in 100 ml of ether and 6 ml of 5 N hydrogen chloride in ether were added thereto. The mixture was vacuum filtered and the recovered product was crystallized from methanol to obtain 5.3 g of the hydrochloride of the base melting at 250° C.

Analysis: $C_{24}H_{29}ClN_2O_4$
Calculated: %C: 64.78; %H; 6.57; %Cl: 7.97; %N: 6.30; Found: %C: 64.6; %H; 6.4; %Cl: 7.8; %N: 6.3.

EXAMPLE 5

(dl) erythro 1,3-dihydro-3-{1-[2-(2,3-dihydro-1,4-benzodioxin-2-yl)-2-hydroxyethyl]-piperidin-4-yl}-5-methoxy-2H-indol-2-one hydrochloride

STEP A:
1,3-dihydro-5-methoxy-3-(1-benzyl-piperidin-4-ylidene)-2H-indol-2-one Ammonia was bubbled for one hour through a mixture of 10 g of 1,3-dihydro-5-methoxy-2H-indol-2-one, 200 ml of ethanol and 20 ml of N-benzyl-4-piperidone and the mixture was heated at 90° C. for 4 hours and then stood overnight at room temperature. The mixture was diluted with water and was extracted with methylene chloride. The organic phase was washed with water, dried and evaporated to dryness and the residue was chromatographed over silica gel. Elution with a 6-3-1 cyclohexane-chloroform-triethylamine mixture yielded 12.4 g of 1,3-dihydro-5-methoxy-3-(1-benzyl-piperidin-4-ylidene)-2H-indol-2-one melting at 152° C.

STEP B:
1,3-dihydro-5-methoxy-3-(piperidin-4-yl)-2H-indol-2-one

A stirred mixture of 14 g of the product of Step A, 140 ml of acetic acid and 1.4 g of 9.6% palladized carbon was heated at 50° C. while saturated with hydrogen and when hydrogen absorption ceased, the mixture was filtered. The filtrate was evaporated to dryness and the residue was taken up in water. The aqueous phase was made alkaline with sodium hydroxide and the mixture was extracted with methylene chloride. The organic phase was washed with water, dried and evaporated to dryness to obtain 8.5 g of raw product. The latter was chromatographed over silica gel and was eluted with an 85-10-5 chloroform-methanol-triethylamine mixture to obtain 1,3-dihydro-5-methoxy-3-(piperidin-4-yl)-2H-indol-2-one with a Rf=0.15.

STEP C: (dl) erythro
1,3-dihydro-3-{1-[2-(2,3-dihydro-1,4-benzodioxin-2-yl)-2-hydroxyethyl]-piperidin-4-yl}-5-methoxy-2H-indol-2-one hydrochloride A mixture of 9.85 g of the product of Step B, 8.6 g of erythro 2-oxyranyl-1,4-benzodioxin, 100 ml of anhydrous benzene and 5 ml of methanol was refluxed for 3 hours and was then evaporated to dryness under reduced pressure. The residue was chromatographed over silica gel and was eluted with a 95-5 methylene chloride-methanol mixture. The product was crystallized from ether to obtain 14.2 g of (dl) erythro 1,3-dihydro-3-{-1-[2-(2,3-dihydro-1,4-benzodioxin-2-yl)-2-hydroxyethyl]-piperidin-4-yl}-5-methoxy-2H-indol-2-one melting at 110° C. (pasty melt).

Analysis:
Calculated: %C: 67.89; %H: 6.65; %N: 6.60; Found: %C: 67.1; %H: 6.6; %N: 6.5.

NMR Spectrum (deuterochloroform—60 MHz): peaks at 201–203 Hz (hydrogen of nitrogen ring); at 220 to 270 Hz (CH$_2$O and —CHO); at 228 Hz (OCH$_3$); at 405 to 411 Hz (aromatics).

The said base was dissolved in 100 ml of methylene chloride and 10 ml of 4 N hydrochloric acid and then 200 ml of anhydrous ether were added thereto. The mixture was vacuum filtered and the recovered product was washed with ether and dried to obtain 11.8 g of the hydrochloride of the said base melting at 150° C. (pasty fusion).

PHARMACOLOGICAL DATA

A. Hypotensive Activity

The hypotensive activity was determined on groups of male rats of the Sprague Dawley S.P.F. strain weighing about 300 g which had been anesthesized with an intraveinous administration of 50 mg/kg of nembutal. The test products in their hydrochloride form were administered intraveinously in the jugular vein and the carotidiene arterial pressure was measured before and after the said administration. The variations between the initial arterial pressure and the pressure after the administration was determined as well as the time of duration of the activity and the results are reported in Table I.

TABLE I

| Product of Example | Dose in mg/kg | % variation of material pressure | Duration of activity in min. |
|---|---|---|---|
| 1 | 1 | −20 | 1 |
|   |   | −10 | 45 |
| 2 | 1 | −30 | 5 |
|   |   | −20 | 60 |
| 3 | 1 | −20 | 1 |
|   |   | −10 | 15 |
| 4 | 1 | −28 | 1 |
|   |   | −23 | 5 |
|   |   | −26 | 10 |
|   |   | −24 | 30 |

B. Antihypertensive Activity

The antihypertensive activity was determined on spontaneous hypertendus male rats of the Okamto strain about 8 weeks old and the test products were orally administered in the hydrochloride form over 9 days. The arterial pressure was measured before and after the said administration on the rat's tail with a pneumatic collar connected to an electronic translator of pressure and the results of Table II compare the initial arterial pressure with the arterial pressure 1,4 hours of the first day and 24 hours after the last administration.

TABLE II

| Product of Example | Dose in mg/kg | % Variation of arterial pressure hours after administration | | |
|---|---|---|---|---|
|   |   | 1 | 4 | 10th day |
| 1 | 50 | −29 | −27 | −8 |
| 2 | 50 | −23 | −22 | −9 |
| 4* | 50 | −23 | −31 | −16 |

*test was for 3 days administration

C. Acute Toxicity

The acute toxicity of the products was determined on groups of 10 mice weighing between 18 and 22 g and the products were intraperitoneally administered in a suspension in carboxymethyl cellulose. The animals were observed for one week to determine the LD$_{50}$ dose at which 50% of the animals died.

TABLE III

| Product of Example | LD$_{50}$ in mg/kg |
|---|---|
| 1 | ≈ 150 |
| 2 | ≈ 125 |
| 3 | ≈ 125 |
| 4 | ≈ 200 |

Various modifications of the products and processes of the invention may be made without departing from the spirit or scope thereof and it is to be understood that the invention is to be limited only as defined in the appended claims.

We claim:

1. A compound selected from the group consisting of optically active isomers or racemates of 1,3-dihydro-3-{1-[2-(2,3-dihydro-1,4-benzodioxin-2-yl)-2-hydroxyethyl]-piperidin-4-yl}-2H-indol-2-ones of the formula

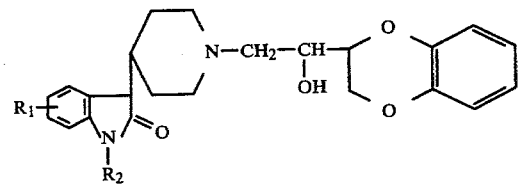

wherein R$_1$ is selected from the group consisting of hydrogen, chlorine, bromine, fluorine and alkoxy of 1 to 5 carbon atoms and R$_2$ is selected from the group consisting of hydrogen and alkyl of 1 to 5 carbon atoms and their non-toxic, pharmaceutically acceptable acid addition salts.

2. A compound of claim 1 wherein R$_1$ is selected from the group consisting of hydrogen, chlorine and methoxy and R$_2$ is selected from the group consisting of hydrogen and methyl.

3. A compound of claim 1 selected from the group consisting of optical isomers and racemates of erythro 1,3-dihydro-3-{1-[2-(2,3-dihydro-1,4-benzodioxin-2-yl)-2-hydroxyethyl]-piperidin-4-yl}-2H-indol-2-one and its hydrochloride.

4. A compound of claim 1 selected from the group consisting of optical isomers and racemates of threo 1,3-dihydro-3-{1-[2-(2,3-dihydro-1,4-benzodioxin-2-yl)-2-hydroxyethyl]-piperidin-4-yl}-2H-indol-2-one and its hydrochloride.

5. A compound of claim 1 selected from the group consisting of optical isomers and racemates of erythro 1,3-dihydro-3-{1-[2-(2,3-dihydro-1,4-benzodioxin-2-yl)-

2-hydroethyl]-piperidin-4-yl}-1-methyl-2H-indol-2-one and its hydrochloride.

6. A compound of claim 1 selected from the group consisting of optical isomers and racemates of erythro-1,3-dihydro-3-{1-[2-(2,3-dihydro-1,4-benzodioxin-2-yl)-2-hydroxyethyl]-piperidin-4-yl}-5-methoxy-2H-indol-2-one and its hydrochloride.

7. An antihypertensive composition comprising an antihypertensively effective amount of at least one compound of claim 1 and an inert pharmaceutical carrier.

8. A composition of claim 7 wherein $R_1$ is selected from the group consisting of hydrogen, chlorine and methoxy and $R_2$ is selected from the group consisting of hydrogen and methyl.

9. A composition of claim 7 selected from the group consisting of optical isomers and racemates of erythro 1,3-dihydro-3-{1-[2-(2,3-dihydro-1,4-benzodioxin-2-yl)-2-hydroxyethyl]-piperidin-4-yl}-2H-indol-2-one and its hydrochloride.

10. A composition of claim 7 selected from the group consisting of optical isomers and racemates of threo 1,3-dihydro-3-{1-[2-(2,3-dihydro-1,4-benzodioxin-2-yl)-2-hydroxyethyl]-piperidin-4-yl}-2H-indol-2-one and its hydrochloride.

11. A composition of claim 7 selected from the group consisting of optical isomers and racemates of erythro 1,3-dihydro-3-{1-[2-(2,3-dihydro-1,4-benzodioxin-2-yl)-2-hydroyethyl]-piperidin-4-yl}-1-methyl-2H-indol-2-one and its hydrochloride.

12. A composition of claim 7 selected from the group consisting of optical isomers and racemates of erythro 1,3-dihydro-3-{1-[2-(2,3-dihydro-1,4-benzodioxin-2-yl)-2-hydroxyethyl]-piperidin-4-yl}-5-methoxy-2H-indol-2-one and its hydrochloride.

13. A method of relieving hypertension in warm-blooded animals comprising administering to warm-blooded animals an antihypertensively effective amount of at least one compound of claim 1.

14. A method of claim 13 wherein $R_1$ is selected from the group consisting of hydrogen, chlorine and methoxy and $R_2$ is selected from the group consisting of hydrogen and methyl.

15. A method of claim 13 wherein the compound is selected from the group consisting of optical isomers and racemates of erythro 1,3-dihydro-3-{1-[2-(2,3-dihydro-1,4-benzodioxin-2-yl)-2-hydroxyethyl]-piperidin-4-yl}-2H-indol-2-one and its hydrochloride.

16. A method of claim 13 wherein the compound is selected from the group consisting of optical isomers and racemates of threo 1,3-dihydro-3-{1-[2-(2,3-dihydro-1,4-benzodioxin-2-yl)-2-hydroxyethyl]-piperidin-4-yl}-2H-indol-2-one and its hydrochloride.

17. A method of claim 13 wherein the compound is selected from the group consisting of optical isomers and racemates of erythro 1,3-dihydro-3-{1-[2-(2,3-dihydro-1,4-benzodioxin-2-yl)-2-hydroxyethyl]-piperidin-4-yl}-1-methyl-2H-indol-2-one and its hydrochloride.

18. A method of claim 13 wherein the compound is selected from the group consisting of optical isomers and racemates of erythro 1,3-dihydro-3-{1-[2-(2,3-dihydro-1,4-benzodioxin-2-yl)-2-hydroxyethyl]-piperidin-4-yl}-5-methoxy-2H-indol-2-one and its hydrochloride.

* * * * *